United States Patent
Arnett

(10) Patent No.: US 6,200,278 B1
(45) Date of Patent: Mar. 13, 2001

(54) GENDER SPECIFIC SOFT TISSUE CEPHALOMETRIC ANALYSIS FOR DIAGNOSIS AND CEPHALOMETRIC TREATMENT PLANNING OF FACIAL IMBALANCE

(75) Inventor: G. William Arnett, Santa Barbara, CA (US)

(73) Assignee: Arnett Facial Reconstruction Courses, Inc., Santa Barbara, CA (US)

( * ) Notice: Subject to any disclaimer, the term of this patent is extended or adjusted under 35 U.S.C. 154(b) by 0 days.

(21) Appl. No.: 09/394,735

(22) Filed: Sep. 13, 1999

Related U.S. Application Data

(63) Continuation-in-part of application No. 09/128,378, filed on Aug. 3, 1998, now Pat. No. 5,951,498.
(60) Provisional application No. 60/062,433, filed on Oct. 16, 1997.

(51) Int. Cl.$^7$ .................................................. A61B 5/103
(52) U.S. Cl. ............................................................ 600/587
(58) Field of Search .................................... 600/587, 589, 600/595

(56) References Cited

PUBLICATIONS

Arnett, et al., The International Journal of Adult Orthodontics & Orthognathic Surgery, 1998, vol. 13, No. 4, Quintessence Publishing Co., Inc.

Arnett, et al., Kephalometrische Analyse der Weichgewebe: Diagnose und Behandlung vertikaler Abweichungen, 1998, IOK, 30.JAHRG., Nr. 2, Germany (this is the German equivalent of the U.S. Journal above).

Arnett, Revista do Straight Wire Brasil de Ortodontia, vol. X11, No. 12, Brazil (this is the Portuguese summary of the U.S. Journal above).

*Primary Examiner*—Cary O'Connor
*Assistant Examiner*—Pamela L Wingood
(74) *Attorney, Agent, or Firm*—Christie, Parker & Hale, LLP

(57) ABSTRACT

A method of soft tissue cephalometric analysis for diagnosis and a method for cephalometric planning treatment for aesthetic correction of facial imbalance in a patient. Normal size, distance, and angle ranges and harmony values of various facial landmarks of aesthetically pleasing faces from a population group are established. The patient will place his or her head in a natural head position. Markers will be placed on soft tissue landmarks and an image will be taken of the patient's head. A true vertical line will be established, and soft and hard tissue landmarks will be measured to the true vertical line. Dentoskeletal measurements will be taken of the face. Finally, in the method of cephalometric planning treatment necessary orthodontic and orthognathic action will be taken to bring measurements into normal range to improve facial balance and aesthetics.

15 Claims, 10 Drawing Sheets

Soft tissue structures
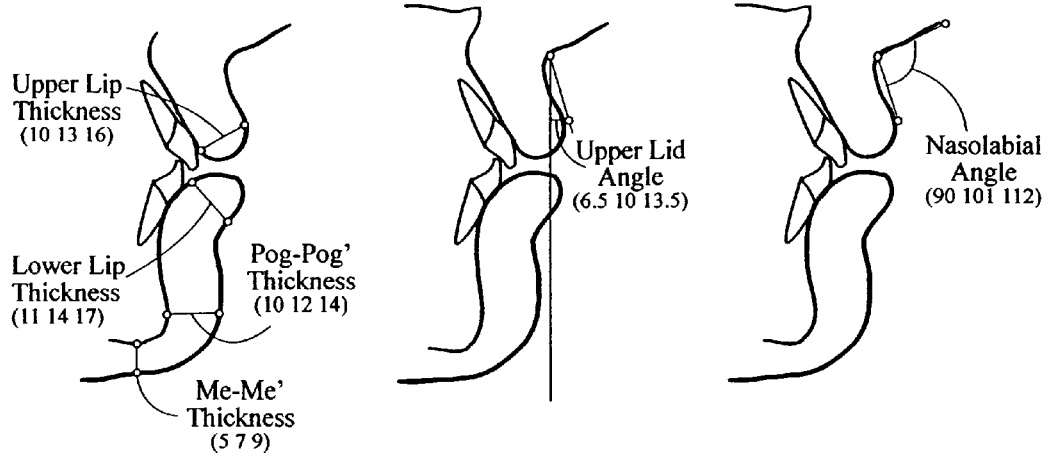
*Figure 4A*  *Figure 4B*  *Figure 4C*
Facial Lengths
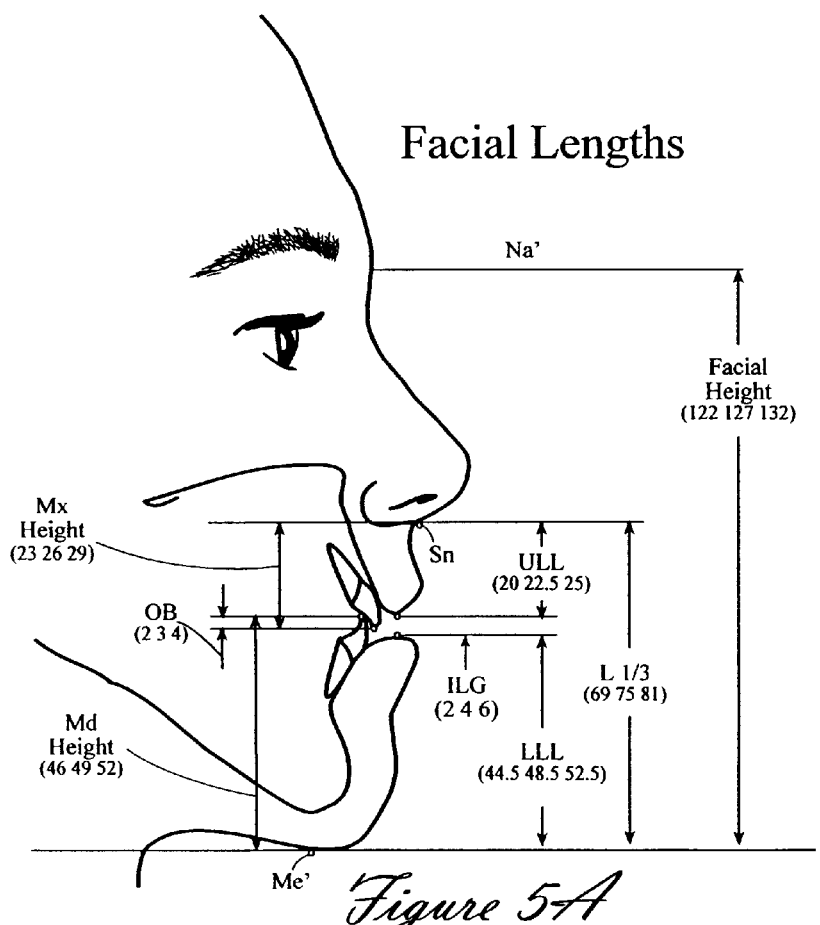
*Figure 5A*

Harmony Values

| Variable | Normal | Dashed | Solid |
|---|---|---|---|
| Mx1 to MxOP | 50 to 58 | 62** | 54 |
| Md1 to MdOP | 60 to 68 | 54** | 64 |
| MxOP to TVL | 91 to 99 | 103** | 95 |

*Figure 12A*

| Variable | Normal | Dashed | Solid |
|---|---|---|---|
| Soft A' | -3.5 to 1.5 | 2 | -1 |
| ULA | .5 to 5.5 | 4 | 3 |
| LLA | -1 to 4 | -1* | 1 |
| Soft B' | -2.5 to 7.5 | -11** | -6 |
| Soft Pgg' | -5.5 to .5 | -7** | -3 |

*Figure 12B*

| Variable | Normal | Dashed | Solid | Facial |
|---|---|---|---|---|
| Angle | 163 to 72 | 160* | 169 | |
| Sn to Pog' | .5 to 5.5 | 9** | | 3 |
| A' to B' | 1.5 to 6.5 | 11** | | 5 |
| ULA to LLA | -1 to 4 | 5* | | 2 |

*Figure 12C*

GENDER SPECIFIC SOFT TISSUE CEPHALOMETRIC ANALYSIS FOR DIAGNOSIS AND CEPHALOMETRIC TREATMENT PLANNING OF FACIAL IMBALANCE

CROSS-REFERENCE TO RELATED APPLICATION(S)

This is a continuation-in-part of application Ser. No. 09/128,378, filed Aug. 3, 1998, now U.S. Pat. No. 5,951,498 which was based upon provisional patent application Ser. No. 60/062,433, filed Oct. 16, 1997, both of which are incorporated by reference as if set forth herein in full.

FIELD OF THE INVENTION

The invention relates generally to the field of cephalometric analysis, and particularly to a method of cephalometric analysis that focuses on soft tissue landmarks as opposed primarily to hard tissue landmarks. The method of soft tissue analysis is called Soft Tissue Cephalometric Analysis (STCA). Additionally, the invention involves a method of Cephalometric Treatment Planning (CTP) used in conjunction with STCA which is designed to achieve consistently excellent outcomes in orthodontics and orthognathic surgery. Orthodontics is utilized to correct bite problems while orthognathic surgery corrects the malalignment of facial bones. Both of these fields, or any field, which deals with facial parts and position can benefit from STCA and CTP.

BACKGROUND OF THE INVENTION

The study of facial aesthetics is not new. Philosophers and artists have struggled for centuries to identify the concrete structural relationships that create an aesthetically pleasing face. Relationships and proportions for pleasing facial contours are well understood, but only in general terms.

Facial attractiveness, while innately recognizable by lay people and artists, has in the past been difficult to quantify. However, it is understood that facial attractiveness can be defined by at least two main facial characteristics, namely quality of facial parts and position of facial parts. The quality of the eyes, skin, the hair, and lips alter the perception of what is beautiful. Cosmetology and the fashion industry (and to a certain extent medicine by dermatology and chemical skin peels to improve the color, tone, smoothness of the skin) are founded upon improving these qualities.

The position of the facial parts also greatly impacts the perception of beauty. The spatial position of the cheekbones, orbital rims, nose, lips, and chin represents position of parts. Surgeons and orthodontists change the position of facial parts with treatment.

In the past, treatment has focused exclusively on bite correction and not on associated facial changes. Historically, treating doctors have relied on model analysis and cephalometric analysis to treatment plan occlusal changes. It has been assumed that correction of model and cephalometric abnormalities would lead to facial balance.

Experience reveals that model diagnosis is incomplete. Model examination identifies interjaw occlusal discrepancies but does not indicate which jaw is abnormally placed. Because of this, model-based bite correction can create facial decline. A study of US orthodontists published in 1993 revealed that 54.9 percent of all orthodontic treatment decisions were based on model examination without other diagnostic modalities. Multiple orthodontic studies have shown facial decline as a result of bite correction based on model analysis. This indicates the need for a reliable facial examination tool such as the STCA.

Cephalometrics emerged in an attempt to quantify the position of parts and thus define facial aesthetics, and has become very well established. The traditional cephalometric method is objective but suffers from measurement of the wrong art of the human anatomy. While facial bones are not normally seen as the essence of beauty, this is what cephalometrics has focused upon-the study of facial bones and their relationship to each other. Unfortunately, errors in diagnosis and treatment planning occur by using osseous cephalometric norms to guide facial outcomes.

Indeed, treatment based on cephalometric hard tissue diagnosis may create undesirable facial change depending on which method of cephalometric analysis is used. Multiple studies have concluded that no correlation exists between traditionally osseous cephalometric treatment planning and facial balance and beauty. Moreover, when different cephalometric analyses are used for skeletal anomalies, as shown in FIG. 1 (note the excess incisor exposure, interlabial gap, and class II profile) and FIG. 2 (note lip redundancy, absence of incisor exposure or interlabial gap, and Class III profile secondary to overclosure of the mandible) respectively, different diagnoses are indicated. Some of these traditional cephalometric analyses are set forth in Tables I and II, resulting in a different diagnosis, different treatment plan, and therefore different outcomes (see indicated treatment movements at bottom of (Tables I and II).

To assure that occlusal treatment favorably alters the position of facial parts, there accordingly remains a strong need for an objective method of cephalometric analysis. This analysis should lead to a complete and full understanding of the various positions and relationships of the various structures of the face and head. Furthermore, information from this analysis should provide a method of cephalometric treatment planning of the soft tissues as well as bite correction.

SUMMARY OF THE INVENTION

One object of the invention is to provide a method of cephalometric analysis that focuses on soft tissue landmarks as opposed primarily to hard tissue landmarks, Soft Tissue Cephalometric Analysis (STCA) and a method of Cephalometric Treatment Planning (CTP) used in conjunction with STCA, to achieve consistently excellent outcomes in orthodontic and orthognathic correction of facial imbalance.

Another object of the invention is to provide health care professionals with a discrete treatment plan to guide in precisely what action must be taken to improve facial balance.

Yet another object of the invention is to provide a gender specific method of soft tissue cephalometric analysis for diagnosis and cephalometric treatment planning of facial imbalance to account for differences between the faces of men and women.

These objects of the invention are carried out by establishing normal size, distance, and angle ranges of various facial landmarks of aesthetically pleasing faces from a population group, having a patient placing his or her head in a natural head position, establishing the true vertical line, measuring soft and hard tissue landmarks to the true vertical line, defining dentoskeletal measurements for the face, and then making necessary orthodontic and orthognathic corrections to improve facial balance and aesthetics.

DESCRIPTION OF THE DRAWINGS

FIGS. 4A–C depict soft tissue structures. Three measurements are listed for each factor (low normal-mean-high normal).

FIGS. 5A–B depict key facial lengths. Three measurements are listed for each factor (low normal-mean-high normal).

FIGS. 12A–D are charts and profiles showing appropriate and inappropriate treatment.

FIG. 13A—Original class II malocclusion with STCA revealing mandibular retrusion. FIG. 13B—Mandibular retrusion treated with inappropriate incisor inclinations and occlusal plane. FIG. 13C—Mandibular retrusion treated with appropriate incisor inclinations and occlusal plane.

Figure 1:
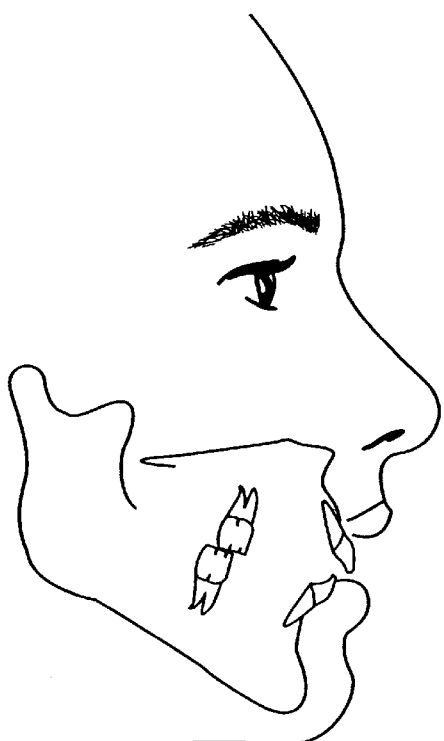
FIG. 1 is a profile view depicting Vertical Maxillary Excess.
Figure 2:
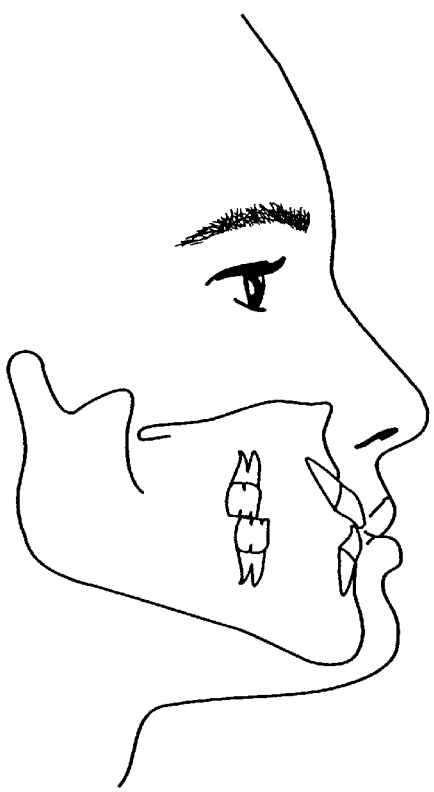
FIG. 2 is a profile view depicting Vertical Maxillary Deficiency.

Table I sets forth a comparison of six commonly used cephalometric analyses of vertical maxillary excess.

Table II sets forth a comparison of six commonly used cephalometric analyses of vertical maxillary deficiency.

Table III sets forth the normal soft tissue cephalometric values and harmony values on a gender unsegregated basis.

Table IV sets forth a comparison between male and female for the method of soft tissue cephalometric analysis of the invention for dentoskeletal factors, soft tissue structure, full face balance, facial length, and projections to true vertical line.

Table V sets forth a comparison between male and female for the method of soft tissue cephalometric analysis of the invention for facial harmony, interjaw relationships, and orbit to jaw.

Table VI sets forth a summary of cephalometric treatment planning for females and males.

DETAILED DESCRIPTION OF THE INVENTION

The inventor has developed a new method of cephalometric analysis termed Soft Tissue Cephalometric Analysis (STCA) and a new method of Cephalometric Treatment Planning (CTP) used in conjunction with STCA to achieve consistently excellent dental and facial outcomes. The novelty of the inventor's approach is its emphasis upon soft tissue relationships and the use of gender specific information. The goal of the STCA analysis therefore, is to objectively analyze soft tissue relationships and subsequently, the relationship between soft tissue and the dentofacial skeleton, to produce consistently attractive orthodontic and orthognathic outcomes. As stated above, model analysis and previous cephalometric analysis have emphasized the measurement of hard tissue landmarks. Orthodontic and orthognathic treatment based on hard tissue measurement has not produced consistently good facial balance.

Specific features of the present STCA analysis include the following: 1) Utilizing postural head position, 2) relaxed lip posture, 3) seated condyle position, 4) first tooth contact 5) use of radiopaque spheres to objectify soft tissue landmarks in the mid-face, 6) a movable True Vertical Line (TVL) which allows measurement of key facial parts, and 7) five groups of measurement (dentoskeletal factors, soft tissue structures, facial lengths, projections, and harmony values) of the face and dentoskeletal structures.

As a result of this analysis, aesthetic goals of occlusal treatment may now be addressed with more objectivity, more accuracy and with treatment plans that are individuated to each patient's need for achieving soft tissue balance.

Perhaps most significantly, aesthetic goals will now be the primary determinate of hard tissue movements instead of being the secondary afterthoughts of occlusal corrections. New knowledge of an individual's facial balance gained from STCA will allow orthodontic and orthognathic treatment to facilitate improved facial results.

Materials And Methods

Thirty-one adult Caucasian models comprise the cephalometric database for this analysis (11 male, 20 female). The model cephalograms were digitized utilizing Quick Ceph Image Pro™, by Quick Ceph of San Diego, Calif. Other programs can be used, or the analysis can be done manually if desired. All models were natural Class I occlusion and viewed by the lead author as facially balanced. A distinction was made during selection between quality of facial parts (hair, eyes, skin, etc.) and position of facial parts. The lead author chose models for inclusion based only on balance of facial parts and disregarded quality of parts (i.e. beautiful eyes).

To initiate the Soft Tissue Cephalometric Analysis, the patients were first assessed clinically according to Arnett and Bergman, in natural head position, uppermost condyle, and with passive lips. See Arnett G W and Bergman R T. Facial keys to orthodontic diagnosis and treatment planning. Part I. Am J Orthod Dentofac Orthop 1993; 103(4):299–312; and Arnett G W and Bergman R T. Facial keys to orthodontic diagnosis and treatment planning. Part II. Am J Orthod Dentofac Orthop 1993; 103(5):395–411, the contents of which are incorporated herein by reference.

Proper clinical exam posturing was imperative to insure the reliability of the soft tissue cephalometric analysis that followed. The STCA was not used without clinical input—it required clinical facial assessment to augment and elucidate cephalometric findings. First, facial examination was employed with particular emphasis on midface structures which do not show on standard cephalometric analysis. In particular, nasal projection, alar base, and upper lip support were noted to indicate anteroposterior position of the maxilla.

Next, in preparation for the cephalometric radiograph, metallic markers were placed on the right side of the face to mark key midface structures. The metallic beads were placed on the models midface using the following routine. The orbital rim marker was placed directly over the osseous orbital rim and directly under the pupil while in straightahead gaze. Cheekbone marking required two perspectives. First, while standing at a contralateral 45-degree angle, the malar height of contour was marked with ink. Then, standing directly in front of the patient, a metal bead was placed at the intersection of the malar height of contour ink mark, and a vertical line through outer canthus. The alar base marker was then placed in the deepest depression of the alar base of the nose. The subpupil marker was situated directly below the straight gaze of the pupil. Vertically, the subpupil marker was placed one half the vertical distance between the orbital rim and alar base markers. These essential midface structures, while normally lost on traditional headfilms, were metallically marked on the headfilm and became the cornerstone to our cephalometric midface diagnosis and treatment planning. The neck-throat point was then localized and a metal marker was placed in that position. The neck-throat point is generally considered to be the point at which the throat breaks inferiorly to form the neck.

Finally, with the midface structures marked, a lateral headfilm is obtained with the patient positioned in natural head position, uppermost condyle, and with passive lips. Assuring accurate head position is very important. As indicated by Moorees (Moorrees CFA, Kean MR. Natural Head Position, A Basic Consideration in the Interpretation of Cephalometric Radiographs. Am J Phys Anthropol 1958; 6:213–34) and Cooke (Cooke M S, Wei SHY. The Reproducibility of Natural Head Posture: a Methodological Study. Am J Orthod Dentofac Orthop 1988; 93(4):280–8.), one standard deviation of natural head position is about +2 degrees. This important head position is achieved by asking the patient to look into their own eyes in a mirror placed across the room as described by Moorees and Cooke.

The True Vertical Line was then established. The line was placed through subnasale and was perpendicular to the natural head position horizontal. Soft tissue landmarks, those reported as important in the "Facial Keys" articles were then marked on the cephalogram. The midface metallic landmarks were also identified as new landmarks on the headfilm. Important hard tissue landmarks were then identified on the cephalogram. The soft tissue and hard tissue landmarks were then measured relative to the models natural horizontal head position and TVL. Mean values and standard deviations were calculated (see Table III). For different racial groups, different databases might be compiled. As set forth in Tables IV to VI, there are important statistical differences between men and women as well. The normals and standard deviations for this analysis do not exist in total in any other analysis.

Results

Based on the cephalometric soft and hard tissue landmarks measured on the 31 facially balanced Caucasian models, dentoskeletal, soft tissue, vertical, projection, and facial harmony norms and standard deviations were established. Table III lists the variables, means, and standard deviations on a gender unspecified basis. Table IV lists the variables on a gender segregated basis. Also, for different racial groups, different databases might be compiled. Attractiveness is defined for purposes of the analysis as a mutually agreed upon general sense of attraction or pleasure. (Obviously, there are different cultural, ethnic, and other factors at play that influence the perception and definition of "beauty". Notwithstanding this, by selecting from a group of faces considered aesthetically pleasing, the database will provide valuable insight into standards applicable to the patient's face being examined.)

Examination of mean data revealed that male and female values were within one millimeter for all anteroposterior measurements. However, vertically, the mean values for males were approximately ten percent greater than for females except for incisor exposure and interlabial gap. The female models had slightly more incisor exposure and interlabial gap than the male models.

Turning to Tables V and VI, there is set forth a statistical analysis using t testing comparing male and female for the method of soft tissue cephalometric analysis of the invention for dentoskeletal factors, soft tissue structure, full face balance, facial length, and projections to true vertical line, and for facial harmony, interjaw relationships, and orbit to jaw.

A level of significance of five percent was assigned and p values were determined. As can be seen in Tables IV and V, statistical analysis revealed that males and females are facially similar in some measures but different in others. Dentoskeletal means were not statistically different for males and females. All male soft tissue thicknesses were statistically greater (ANS to Sn, A to A', upper lip thickness, lower lip thickness, Pog to Pog', and Me to Me') than the females. The female models demonstrated more upper lip protrusion indicated by the upper lip angle (+3.8 degrees), and nasolabial angle (−2.9 degrees), the upper lip angle was statistically different while the nasolabial angle was not. Male faces were statistically longer [Na' to Me' (13.1 mm), upper lip length (3.4 mm), lower lip length (7.4 mm), lower ⅓ (10.0 mm), Mx height (2.7 mm), Md height (7.4 mm)] than female faces. The female models had statistically more incisor Mx1 exposure (4.7 mm versus 3.9 mm) and a greater but insignificant (3.3 mm versus 2.4 mm) interlabial gap than the male models. The male and female projection measurements were statistically the same (within 1 mm) except for midface, incisor projections, and P' point. The male orbital rim (−3.7 mm), cheek bone (−4.6 mm), subpupil (−3.2 mm), upper incisor Mx1 (−2.9 mm), lower incisor Md1 (−3.0 mm), and B point values were statistically larger (more negative to the TVL) than the females. Facial harmony values were statistically similar for all but three relationships. The males had statistically different harmony for A' to B', orbital rim' to Pog', and Glabella' to Pog'. With the above noted, the most significant treatment planning difference between males and females is the large vertical differences between the two groups and larger midface measurements for the male.

Clinical Implications

Soft Tissue Cephalometric Analysis provides dental and facial diagnosis. Data provided by the STCA can then be used for Cephalometric Treatment Planning (CTP).

Soft Tissue Cephalometric Analysis Diagnosis

The various initials used herein and in the drawings are as follows:

Mx maxilla
Mx1 maxillary incisor
Md mandible
Md1 mandible incisor
OJ overjet
OB overbite
Pog hard tissue pogonion
Pog' soft tissue pogonion
Me hard tissue menton
Me' soft tissue menton
NL nasolabial
Na' soft tissue nasion
Na hard tissue nasion
ILG interlabial gap G' soft tissue glabella
OR orbital rim
CB cheekbone
SP subpupil
AB alar base
NT nasal tip
Sn subnasale
A' soft tissue A Point
ULA upper lip anterior
LLA lower lip anterior
B' soft tissue B Point
NT neck-throat Point
OP occlusal plane
HV harmony values The STCA can be used to diagnose the patient in five different but interrelated areas; dentoskeletal factors, soft tissue components, facial lengths, true vertical line (TVL) projections, and harmony of parts.

Figure 3:
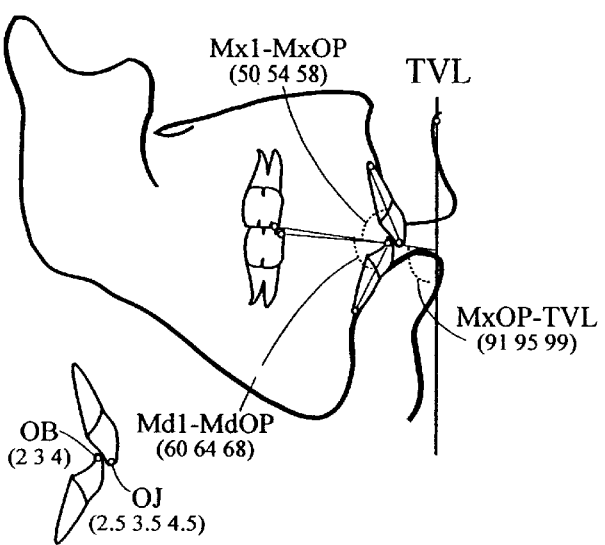
FIG. 3 is a schematic view showing dentoskeletal factors. Three measurements are listed for each factor (low normal-mean-high normal).

Referring to FIG. 3, dentoskeletal factors have a large influence on the facial profile. These factors, when in normal range will usually produce a balanced, harmonious nasal base, lip, soft A', soft B', and chin relationship. How accurately the orthodontist and surgeon manage the dentoskeletal components greatly influences the resulting profile. Ideal profiles are incompatible with incorrect upper and lower incisor inclination, abnormal overbite and overjet, and deviant maxillary occlusal plane. Three measures are given for each factor (low normal-mean-high normal).

A general comment applies with respect to FIGS. 3–13c. The numbers and angles set forth on FIGS. 3–13c are made with respect to the generalized non-gender segregated data of Table III. The numbers for males and female from Tables IV and V apply for females and males, as segregated groups.

Referring to FIG. 4, the soft tissue structures important to facial aesthetics are measured. The thickness of upper lip, lower lip, Pog to Pog', and Me to Me' alter facial profile. Soft tissue thickness in combination with dentoskeletal factors largely control lower facial aesthetic balance. The nasolabial angle and upper lip angle reflect the position of the upper incisor teeth and the thickness of the soft tissue overlying these teeth. These angles are extremely important in assessing the upper lip and may be used by the orthodontist as part of the extraction decision. These soft tissue structures are altered by movement of the incisor teeth. These angles should be studied prior to orthodontic overjet correction to assess the potential for changes out of normal range. They guide the orthodontic extraction decision. Extractions which adversely open the nasolabial (>110) angle or upright the upper lip (<7 degrees to TVL) should be avoided. Three measurements are listed for each factor (low normal-mean-high normal).

Figure 5B:
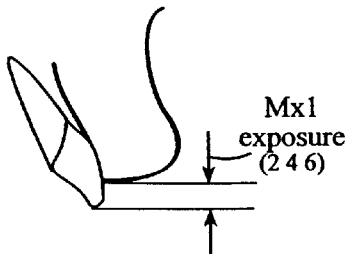

Turning to FIG. 5, the facial lengths are conceptualized as soft tissue facial lengths. Soft tissue lengths include facial height (Na' to Me'), lower one-third height (Sn to Me'), upper lip length (Sn to UL inferior), lower lip length (LL superior to Me'), and interlabial gap (UL inferior to LL inferior). Additional soft tissue to hard tissue measurements include maxillary incisor exposure (UL inferior to maxillary incisor tip), maxillary height (Sn to maxillary incisor tip), and mandibular height (mandibular incisor tip to Me'). The only hard tissue to hard tissue measurements is the overbite. The presence and location of vertical abnormalities is indicated by assessing maxillary height, mandibular height, upper incisor exposure and overbite. Three measurements are listed for each factor (low normal-mean-high normal).

Figure 6:
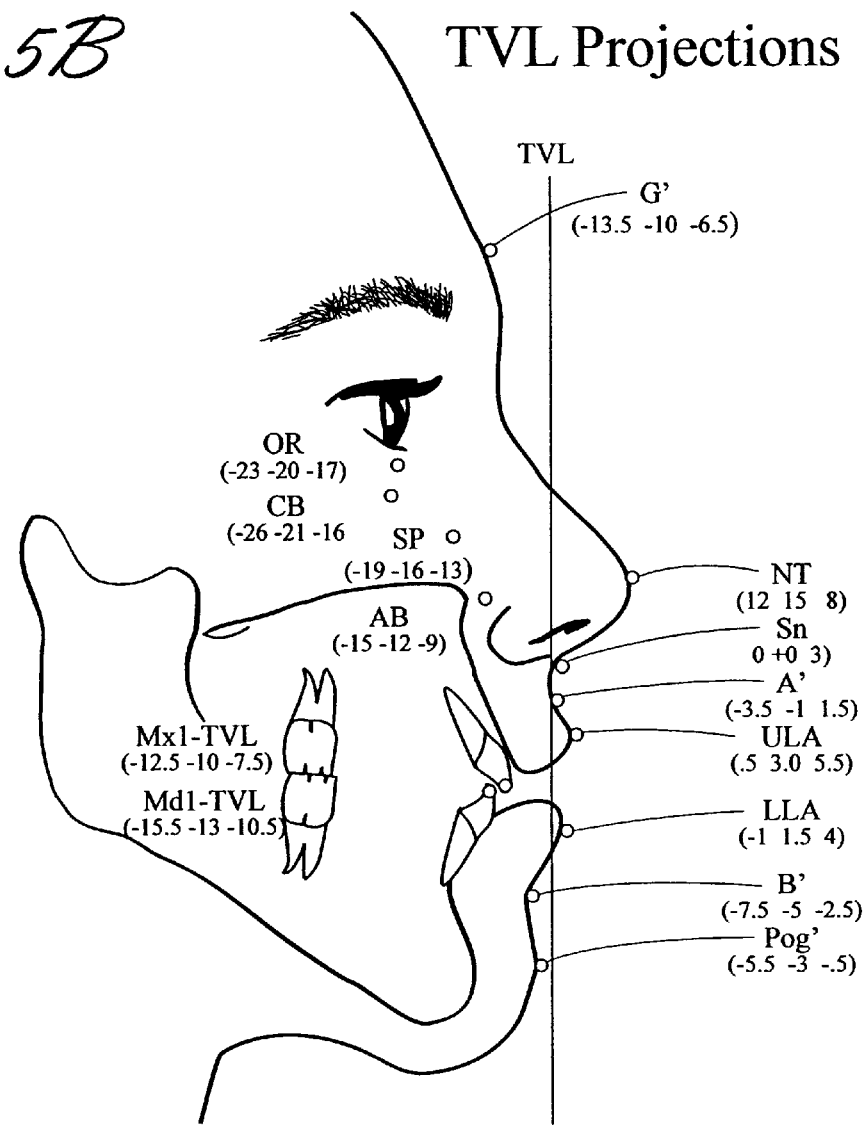
FIG. 6 depicts the TVL projections. Three measurements are listed for each factor (low normal-mean-high normal).

FIG. 6 shows TVL projections that are anteroposterior measurements of soft tissue and represent the sum of the dentoskeletal position plus the soft tissue thickness overlying that hard tissue landmark. The horizontal distance from TVL to each individual landmark is termed the "landmark absolute value." The TVL is generally placed on or near Sn. When midface retrusion is diagnosed the TVL is moved 1–2 mm anterior. Midface retrusion is defined by a long nose, deficient alar base, poor incisor upper lip support, upright upper lip and/or thick upper lip. Profile points measured to TVL are Glabella, nasal tip, soft tissue A' point, upper lip anterior, lower lip anterior, soft tissue B' point, and soft tissue Pogonion'. Midface, nonprofile points measured to the TVL are soft tissue orbital rim, cheekbone height of contour, subpupil, and alar base. Hard tissue measured to the TVL are upper incisor tip and lower incisor tip. Three measurements are listed for each factor (low normal-mean-high normal).

Turning to FIG. 7, harmony values were devised to measure facial structure balance and beauty. Harmony, or balance between different facial landmarks is very important in creating beauty. It is the position of each landmark relative to other landmarks that determines the facial balance. (All values are calculated from the horizontal difference between points as calculated from the TVL. Three measurements are listed for each factor (low normal-mean-high normal.) Harmony values examine four areas of balance-intramandibular parts, interjaw, orbits to jaws, and the total face. The following harmony groupings are essential to excellent dentofacial outcomes.

Figure 7A:
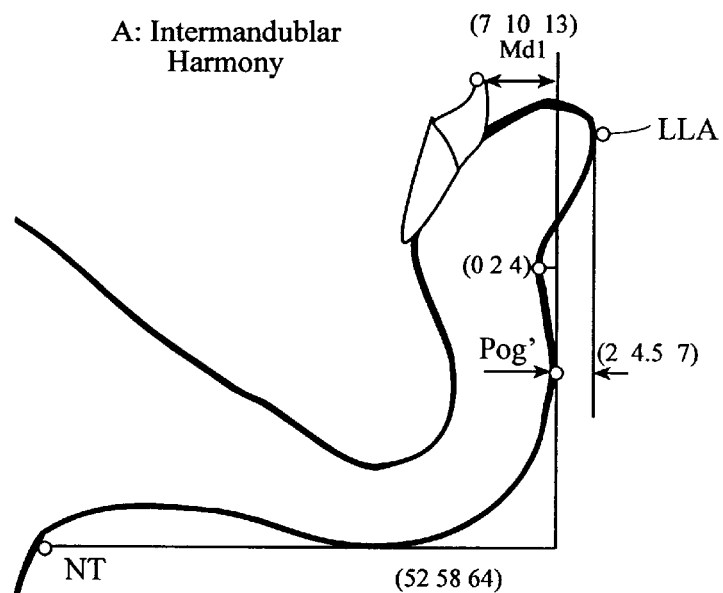
FIGS. 7A–D depicts the Harmony Values (A. Intramandibular harmony, B. Interjaw relationships, C. Orbital rim to jaws, and D. Total face harmony). Three measurements are listed for each factor (low normal-mean-high normal).

Referring to FIG. 7A, intramandibular harmony values assess chin projection (Pog') relative to the lower incisor, lower lip, soft tissue B' point, and the neck throat point. Since isolated chin deformities can be caused by a hypertrophied mental protuberance, procumbent mandibular incisors, displacement by maxillary incisors (as in the case of deep bite malocclusions), or any combination of the above, these issues need to be defined. To completely understand the value of these relations one must give special consideration to the occlusal plane angle. For example, the flatter occlusal plane will accentuate a prognathic chin associated with an enlarged mental protuberance. Conversely, increasing the occlusal plane angle will produce a weak chin and submental soft tissue profile, in those patients with an otherwise normal osseous relationship. Analysis of these structures determines chin position relative to other mandibular structures and which, if any, structure is abnormally placed. For example, excessive distance from mandibular incisor tip to the chin may indicate an upright lower incisor, or hard tissue pogonion enlargement, or increased thickness of the chin soft tissues (Pog to Pog'). All of these possibilities are examined within the intramandibular harmony group and a diagnosis is made so that treatment can be rendered to harmonize structures within the mandible. FIG. 7A depicts lower incisor to Pog', soft tissue B' to Pog', and neck throat point to Pog'.

Figure 7B:
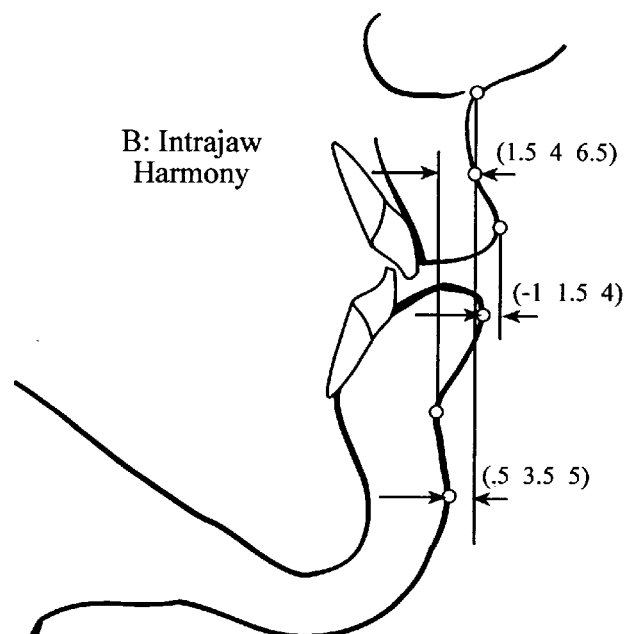

Next, interjaw harmony (as shown in FIG. 7B) is examined. These relationships directly control lower one-third facial aesthetics. These values indicate the interrelationship between the base of the maxilla (Sn) to chin (Pog'), soft tissue B' to soft tissue A' and upper lip anterior to lower lip anterior. Soft tissue thickness, but more importantly, dentoskeletal factors (upper incisor angulation, lower incisor angulation, maxillary occlusal plane), determine interjaw harmony.

Figure 7C:
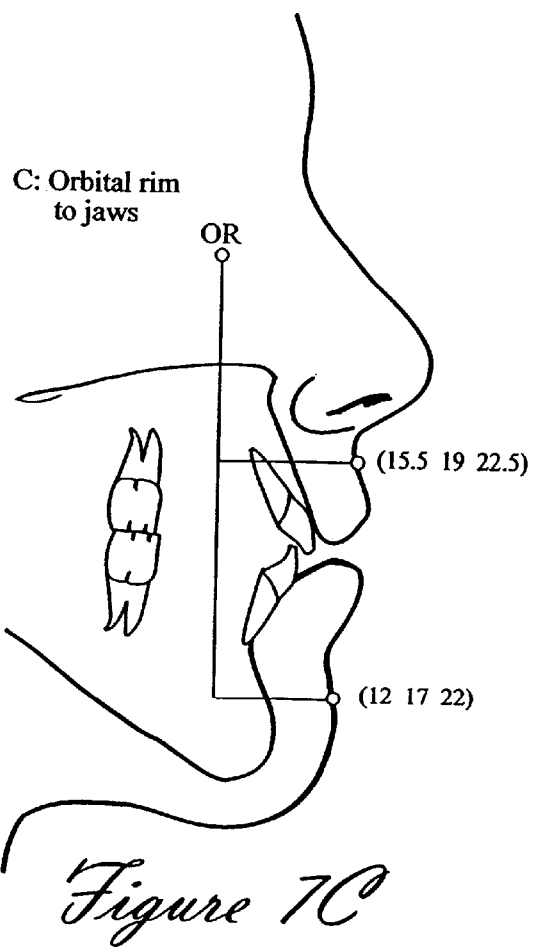

Turning to FIG. 7C, inspection then focuses on orbital rim to jaw harmony. The position of the soft tissue inferior orbital rim relative to the upper jaw (OR'-soft tissue A') and the lower jaw (OR'-Pog') are measured. Measurements between these areas assess high midface to jaw balance. At this point, there is some understanding of how the jaws balance with each other and how the jaws relate to the midface. The evaluation however, is still not complete. The entire facial context has not been considered. The jaws may be in harmony with the orbital rims, but the jaw/orbital rim complex may still be retrusive (or in rare cases, protrusive) in relation to the upper face. Based upon the above measurements and factors alone, an accurate diagnosis still cannot be made.

Figure 7D:
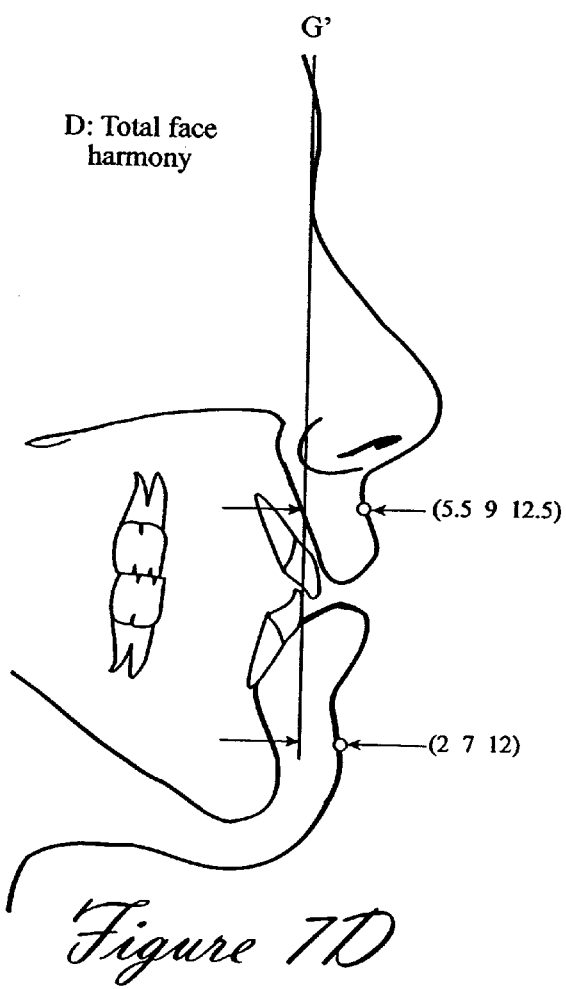

Referring to FIG. 7D, the last step of the harmony examination is total facial harmony. The upper face, midface, and chin are related via the facial angle (G'-Sn-Pog'). The forehead at glabella is then compared to two specific points, the upperjaw (G'-soft tissue A') and chin (G'-Pog'). These three measures give the broad picture of facial balance.

Figure 8:
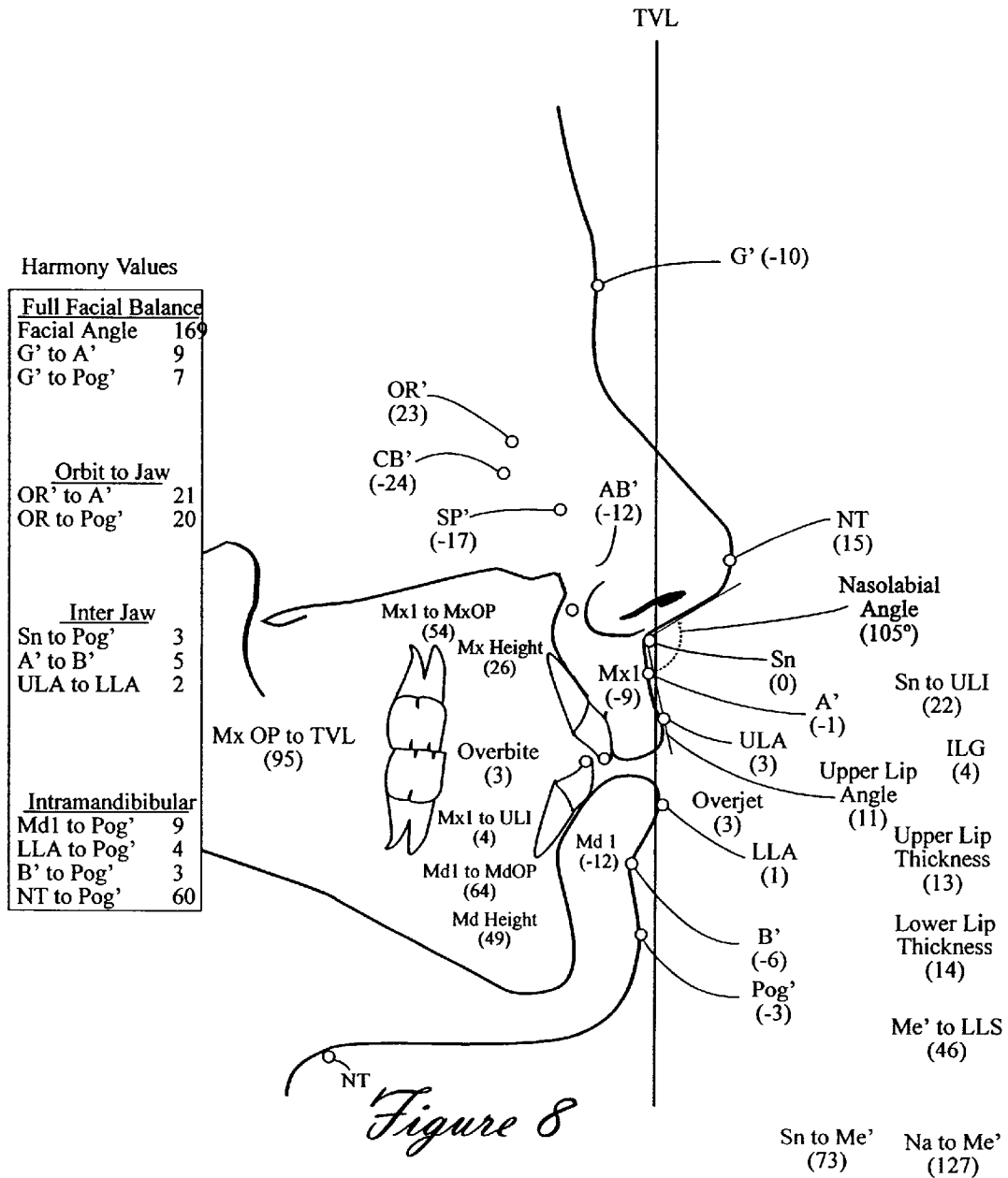
FIG. 8 depicts the complete Soft Tissue Cephalometric Analysis.
Figure 9:
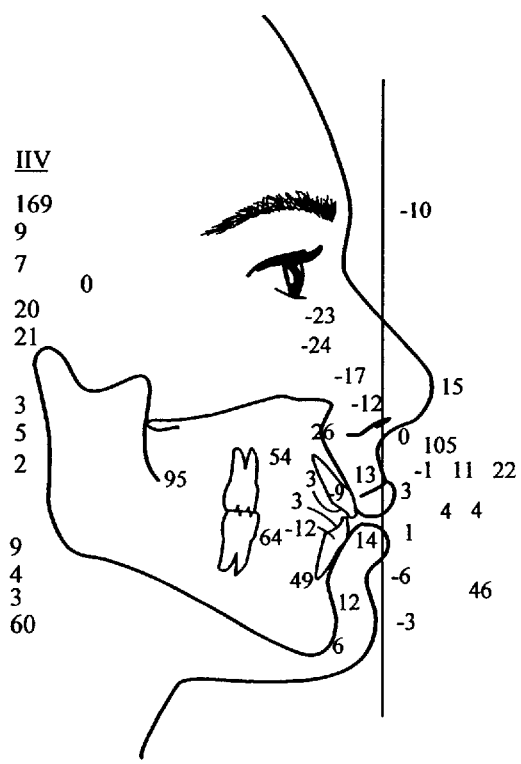
FIG. 9 depicts landmark absolute values.

The complete Soft Tissue Cephalometric Analysis is shown in FIG. 8. Measurements are identified and placed in their standard positions. The soft tissue cephalometric values are measured and printed, for example, within the Quick Ceph Image Pro™ program. Absolute values to the TVL are indicated by their anatomic abbreviation (i.e. A' or ULA). Landmarks that are not associated with TVL line are described (i.e. Mx height, overbite, or Sn to Pog').

FIG. 8 serves as a reference drawing for FIGS. 9–13. All values are within normal range. This soft tissue cephalometric analysis can be done on standard acetate, without computerization (refer to FIG. 8 for landmark and measurement clarification.)

Figure 10:
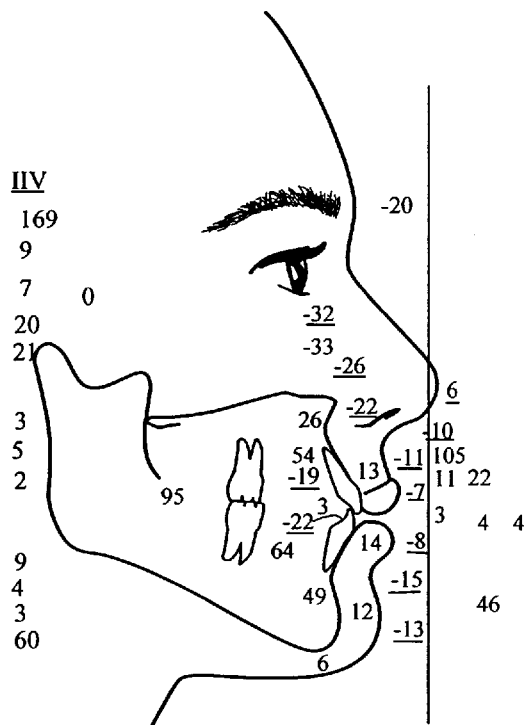
FIG. 10 depicts the patient profile of FIG. 9 but with the true vertical line moved to the right.

The patient profiled in FIG. 9 is again examined in FIG. 10. The TVL used in FIG. 9 has been moved 10.0 millimeters to the right. After moving the TVL, absolute values are primed (2 standard deviations) or underlined (3 standard deviations), reflecting the change in TVL position. Note that the Harmony Values are unchanged from FIG. 9. Harmony values do not change with TVL position change, and are therefore diagnostically reliable. (refer to FIG. 8 for landmark and measurement clarification.) After completing the STCA, the next stage in the regimen of the invention is Cephalometric Treatment Planning (CTP).

Turning now to Tables V and VI, there is set forth a statistical analysis using t testing comparing male and female for the method of soft tissue cephalometric analysis of the invention for dentoskeletal factors, soft tissue structure, full face balance, facial length, and projections to true vertical line, and for facial harmony, interjaw relationships, and orbit to jaw.

A level of significance of five percent was assigned and p values were determined. As can be seen in Tables V and VI, statistical analysis revealed that males and females are facially similar in some measures but different in others. Dentoskeletal means were not statistically different for males and females. All male soft tissue thicknesses were statistically greater (ANS to Sn, A to A', upper lip thickness, lower lip thickness, Pog to Pog', and Me to Me') than the females. The female models demonstrated more upper lip protrusion indicated by the upper lip angle (+3.8 degrees), and nasolabial angle (−2.9 degrees), the upper lip angle was statistically different while the nasolabial angle was not. Male faces were statistically longer [Na' to Me'(13.1 mm), upper lip length (3.4 mm), lower lip length (7.4 mm), lower ⅓ (10.0 mm), Mx height (2.7 mm), Md height (7.4 mm)] than female faces. The female models had statistically more incisor Mx1 exposure (4.7 mm versus 3.9 mm) and a greater but insignificant (3.3 mm versus 2.4 mm) interlabial gap than the male models. The male and female projection measurements were statistically the same (within 1 mm) except for midface, incisor projections, and B' point. The male orbital rim (−3.7 mm), cheek bone (−4.6 mm), subpupil (−3.2 mm), upper incisor Mx1 (−2.9 mm), lower incisor Md1 (−3.0 mm), and B point values were statistically larger (more negative to the TVL) than the females. Facial harmony values were statistically similar for all but three relationships. The males had statistically different harmony for A' to B', orbital rim' to Pog', and Glabella' to Pog'. With the above noted, the most significant treatment planning difference between males and females is the large vertical differences between the two groups and larger midface measurements for the male.

CEPHALOMETRIC TREATMENT PLANNING (CTP) FOR FEMALES AND MALES

A new Cephalometric Treatment Planning (CTP) method, Table VI, has been developed based on and in conjunction with the STCA, Tables III–IV. The reason for and decisions on how and why to orthodontically and surgically alter the dentoskeletal components is based on the STCA, then planned using CTP. Orthodontics, lower jaw surgery, upper jaw surgery, or bimaxillary surgery may correct the malocclusion but with differing facial outcomes. By using STCA and CTP together, the occlusal problems of overbite and overjet are treated within the context of the facial problem, and consistently excellent results will result.

Diagnosis generated by the STCA is used to guide cephalometric treatment planning. Seven steps are involved in CTP to optimize occlusal and facial results. Below is an explanation of Table VI.

1. The initial step of CTP is proper angulation of the lower incisor teeth.

2. The second step of CTP is proper angulation of the upper incisors. When these incisor angles are achieved, the true skeletal overjet is revealed without masking by dental compensations. Correct incisor angulations are necessary for ideal facial outcomes. For instance, if the upper incisor is upright (58) or the lower incisor is procumbant (60) the lower lip, B' point, and Pog' will be retrusive relative to the rest of the face. In this example, the incisor angulations create an undesirable convex profile. These examples describe the significant facial impact the orthodontist has through control of incisor angulations.

3. Next, maxillary incisor positioning, the key to dentofacial reconstruction, is accomplished. The upper incisor is placed so that 3 to 5 mm and preferably 4 to 5 mm of incisor is exposed beneath the relaxed upper lip. Horizontally, the upper incisor is positioned according to a combination of clinical and cephalometric findings. Clinical factors are orbital rim, cheekbone, subpupil, and alar base contours, nasal projection, and upper lip support. Cephalometric factors are upper lip thickness and upper lip angle. The incisors and maxilla should be moved forward when the nose is long, midface contours are flat, the upper lip lacks incisor support, the upper lip is thick, and the angle of the upper lip is upright. If the orbital rims and cheekbones are flat, an onlay graft is necessary to produce simultaneous augmentation on those areas. When the maxillary incisor position is aesthetically correct without treatment, no maxillary surgery is indicated unless other reasons exist (i.e. dual plane occlusion, dissimilar arch form or width, etc.)

4. Autorotation of the mandible to 3 mm of overbite is the next CTP step. When autorotation produces a Class I overjet, this indicates that an isolated LeFort I is the only indicated surgery. If, however, autorotation to 3 mm of overbite leaves a Class II or Class III overjet a mandibular advancement or setback is indicated in Step 5.

5. Then the mandible is moved anteriorly or posteriorly to correct the overjet with the maxillary arch.

6. After the overbite and overjet have been set, the maxillary occlusal plane is defined. Changing the maxillary occlusal plane affects chin position and alar base support. The anterior point of the occlusal plane is the maxillary incisor tip. The anterior point is set to expose the incisor edge as described above (Step 3) under maxillary incisor positioning. The posterior point of the occlusal plane line is the mesial buccal cusp tip of the first molar. In general, the more superiorly the first molar is placed relative to the incisor tip, the more convex and less pleasing the facial profile. The profile is usually optimized when the occlusal plane is normal to the true vertical line, Pog' is normal to the TVL, and alar base change appropriately corrects the existing facial condition.

7. The last step of CTP is chin projection and height assessment. Normal Pog' position to the TVL is −2.6 mm±2.5 mm for females and −3.5 mm±1.8 mm for males. Chin position is adjusted in two ways: with a sliding chin osteotomy or by changing the maxillary occlusal plane to increased or decreased projection. Steepening the occlusal plane decreases chin projection, and flattening the occlusal plane increases chin projection. If the chin has poor contour, the occlusal plane can be steepened allowing a chin augmentation to improve the contour and projection. The mandibular heights (chin height) for males and females are 56.0 mm and 48.6 mm respectively. The ration of maxillary height to mandibular height is essentially one to two—53% for females and 51% for males. A chin osteotomy with lengthening or shortening may be used to normalize chin height.

Figure 11:
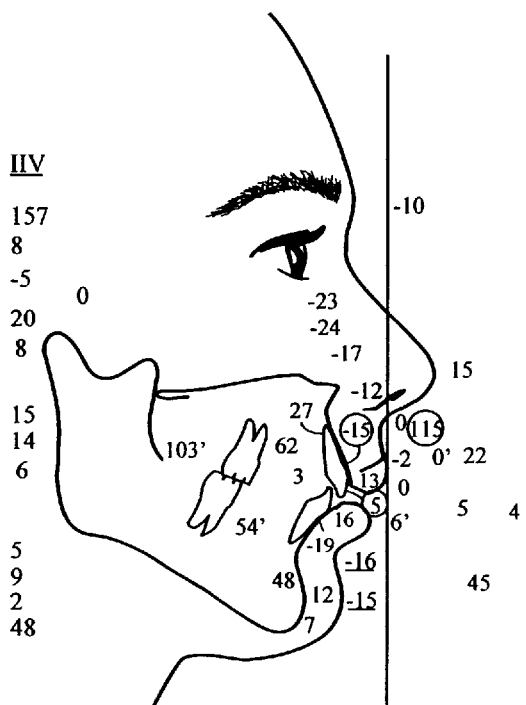
FIG. 11 depicts a patient profile of a Class II malocclusion, with a normal overbite but excessive overjet.

FIG. 11 represents a class II malocclusion patient with abnormal STCA measurements. Class II malocclusion: The overbite is normal (3 mm) but the overjet (5 mm) is excessive. The overjet indicates class II, but does not indicate etiology-maxillary protrusion, vertical maxillary excess, or mandibular retrusion. The STCA is used to identify the etiology as severe mandibular retrusion (Pog' to TVL—15, B' to TVL—16, Md1 to TVL—19, facial angle 157 degrees, G' to Pog' −5, OR' to Pog' 8, Sn to Pog' 15, A' to B' 14, ULA to LLA 6, and NTP to Pog' 48). Other measurements reveal typical compensations associated with mandibular retrusion-steep occlusal plane (MxOP to TVL 103 degrees), upright upper incisors (Mx1 to MxOP 62, Mx1 to TVL −15), obtuse nasolabial angle (115 degrees), upright upper lip (0 degrees), flared lower incisors (Md1 to MdOP 54), and lower lip protrusive relative to Pog' (LLA to Pog' 9). All facial lengths are within normal limits, indicating that the 5 mm overjet is not the result of vertical maxillary excess rotating the mandible down and back. Treatment corrects the malocclusion within the context of the face. (Black=normal range, underlined=one standard deviation, primed=two standard deviations, circled=three standard deviations).

Figure 12D:
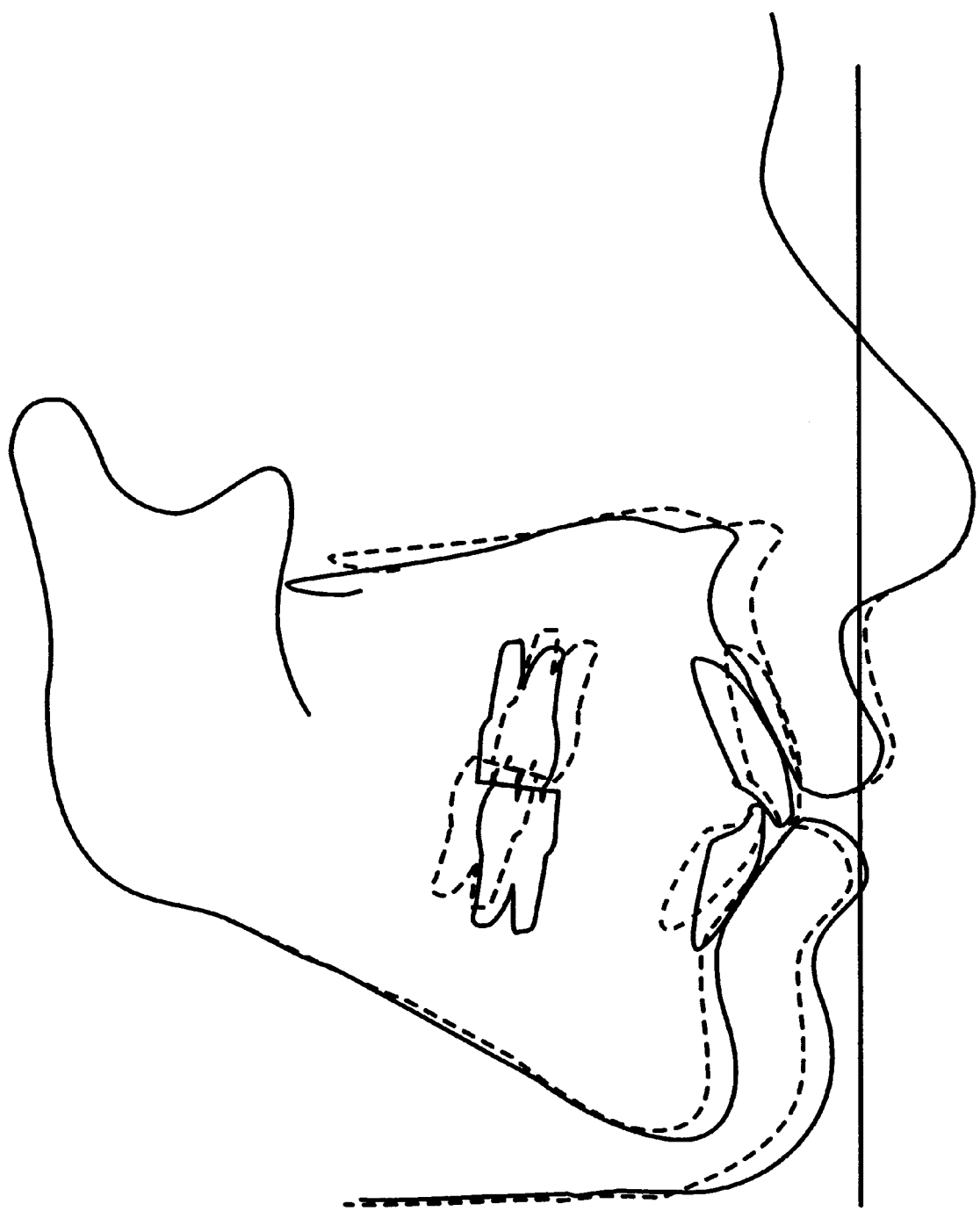

Referring to FIG. 12, the profile differences created by correct and incorrect cephalometric treatment planning for this class II are shown in overlay. Correct presurgical orthodontic preparation produces normal upper and lower incisor angulations. The upper incisor positions are identical. Then, bimaxillary surgery moves the upper incisor to ideal position, normalizes the maxillary occlusal plane, and advances the mandible to correct the overbite and overjet. Ideal CTP and treatment for this patient result in ideal facial changes and normal range STCA values (FIG. 12 [solid lines]). When the same patient is treated to identical upper incisor position (FIG. 12 [dashed line]) but with incorrect incisor angulations and maxillary occlusal plane, poor facial balance results with abnormal STCA values. The only treatment differences are upper and lower incisor inclinations and the occlusal plane (FIG. 12A). These changes produce different profiles (FIG. 12B) and harmony (FIG. 12C)—(*=one standard deviation, **=two standard deviations).

Figure 13A:
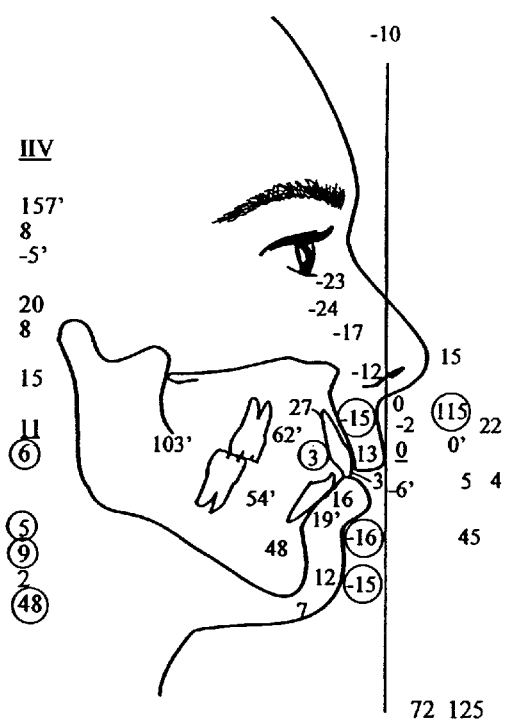
FIGS. 13A–C depict Class II patient STCA profile comparisons.
Figure 13B:
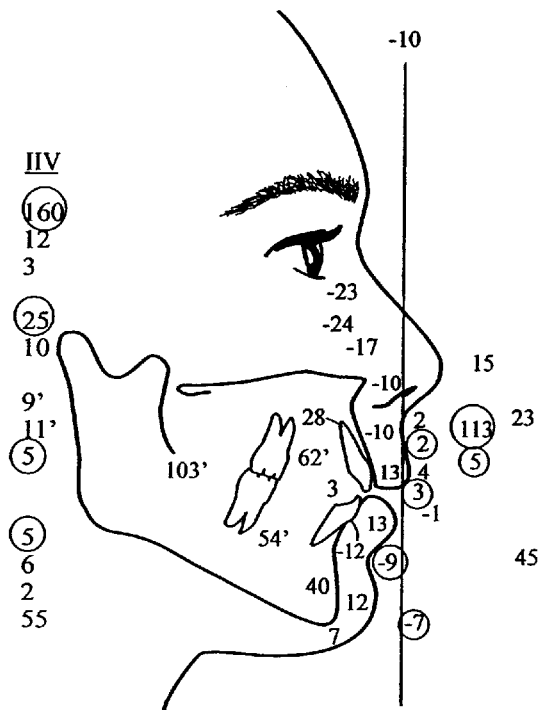
Figure 13C:
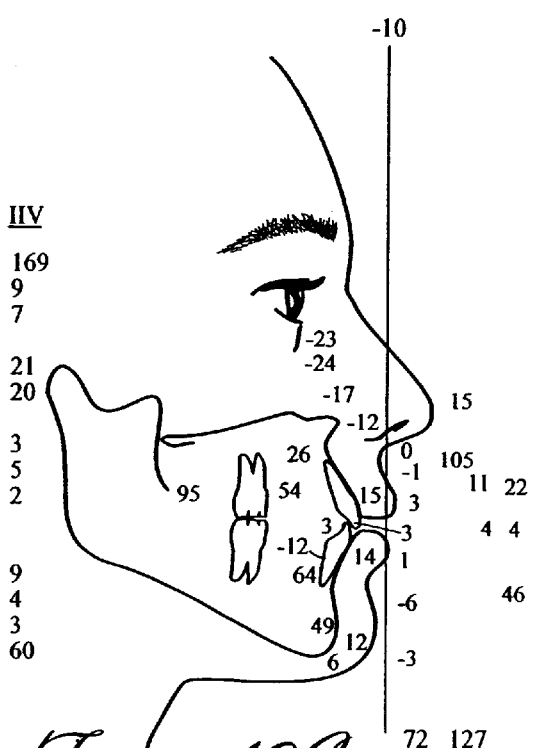

FIGS. 13A–C demonstrates the side-by-side facial STCA for the class II patient (FIG. 13A), incorrect (FIG. 13B), and correct CTP (FIG. 13C). Class II Patient—STCA profile comparisons: FIG. 13A—Original class II malocclusion with STCA revealing mandibular retrusion. FIG. 13B—Mandibular retrusion treated with inappropriate incisor inclinations and occlusal plane. STCA reveals facial imbalance. FIG. 13C—Mandibular retrusion treated with appropriate incisor inclinations and occlusal plane. STCA indicates facial balance (black=normal range, underlined=one standard deviation, primed=two standard deviations, circled=three standard deviations).

Discussion

After the headfilm is obtained, hard and soft tissue cephalometric landmarks can be marked directly by hand on acetate (as in the case of X-ray film), or as was done for this study, digitized into the Quick-Ceph Image Pro™ or other programs. Utilizing the Soft Tissue Cephalometric Analysis, measurements are obtained either manually or by computer. Again, the inventor believes that other presently available technologies (such as technologies which use electronic measuring and capturing of images in lieu of photographic methods) can be used with good results. Although the inventor presently uses a lateral X-ray image (to take a 2-D lateral image), the inventor expects that other technologies can be used to take 2-D images (or even 3-D images) of the patient's head and obtain the appropriate images.

The STCA is a profile tool. As stated previously, the Soft Tissue Cephalometric Analysis is a radiographic instrument that represents the clinical extension of the philosophy detailed in "Facial Keys to Orthodontic Diagnosis and Treatment Planning 1, 2". This cephalometric soft tissue analysis guides soft tissue examination, as do the "Facial Keys" papers, but with added advantages. The original "Facial Keys" papers suggested facial measurement in the clinical setting which is difficult to achieve with accuracy. Because the STCA is cephalometric analysis, profile soft tissue landmarks are easily seen, marked and measured cephalometrically. Importantly, the midface metallic markers, for the first time, allow important soft tissues (orbital rim, cheekbone, subpupil, and alar base) to be easily seen, marked and measured. Additionally, the cephalometric radiograph reveals very important dental and skeletal relationships which the original "Facial Keys" clinical technique did not show (i.e. incisor angulations, maxillary occlusal plane).

The STCA integrates occlusal correction and soft tissue balance. Of the 45 STCA measurements, only five relate hard tissue to hard tissue points-maxillary occlusal plane, maxillary incisor to maxillary occlusal plane, mandibular incisor to mandibular occlusal plane, overbite, and overjet. These hard tissue relationships are measured, because to a large extent, they control the aesthetic outcome of occlusal treatment. The remaining measurements of the STCA emphasize soft tissue dimensions (i.e. upper lip length) or soft tissue to hard tissue dimensions (i.e. upper incisor to upper lip exposure).

The STCA is not meant as a stand-alone cephalometric analysis. It is meant to be used in combination with clinical facial examination and cephalometric treatment planning, providing clinically relevant soft tissue information with checks and balances (harmony values).

In the inventor's study, the natural or postural head position was the horizontal reference. This posture is determined by the patient. It is the position that a person would assume when looking out to a distant object on the horizon. It is the most frequently assumed, the most realistic, and the most reproducible head position. Natural head position has demonstrated a 2 degree standard deviation compared to the 4–6 degree standard deviation for the various cranial based landmarks that are more commonly used.

True vertical line position, as described earlier, can only be established by the clinical and cephalometric examination of the patient. This involves an appraisal of three clinical factors-nasal projection, alar base contour, upper lip support, and two cephalometric measurements-upper lip thickness and angle. These factors establish the TVL line placement used in the STCA. These five factors are also used to determine upper incisor projection during Cephalometric Treatment Planning.

The STCA has five distinct but cross-contributory elements. First, the system analyzes key dentoskeletal structures controlled by the orthodontist (Mx1 to MxOP, Md1 to MdOP) and surgeon (MxOP to TVL). Orthodontic and surgical manipulation of the dentoskeletal factors is key to facial profile and aesthetics. Second, it measures key soft tissue structures that affect facial appearance. Third, it measures important vertical soft tissue lengths and soft tissue to hard tissue relationships. Fourth, it measures soft tissue points relative to the true vertical line, thus producing absolute projection values for each point. Fifth, the absolute values are then related to one another to test facial harmony. Harmony numbers provide a test of facial balance within the individual's face and, importantly, are independent of the true vertical anteroposterior placement. Occasionally with a balanced face, TVL projection values are abnormal secondary to unusual placement of the true vertical line. If this is the case, the harmony values, independent of the true vertical line, will indicate facial balance.

Finally, the use of the STCA develops a more comprehensive understanding of the implications of both orthodontic and surgical treatment. Dental-skeletal relations are very well understood. Skeletal-skeletal interrelationships are also understood. Logically, if skeletal-soft tissue relations are defined, it will now become possible to fully appreciate both the skeletal and dental implications to soft tissue proportion and balance. For instance, with the Soft Tissue Cephalometric Analysis we can appreciate that an upright maxillary central incisor can reduce the projection of the upper lip, lower lip and chin. Additionally, the same upright incisor will produce incorrect harmony between the Sn–Pog', A'–B', and upper and lower lips.

The STCA objectifies important landmarks of the soft tissue envelope. It then objectively relates these structures to the skeleton and teeth. The cephalometric analysis of the past have isolated skeletal regions of a face and measured the degree of disproportion to population norms. This prior method leaves much to be desired. Since this prior method does not measure the soft tissue contour of the face (which is the essence of aesthetics) it is therefore, at best, an educated guess of aesthetics value. The present method of STCA and CTP dictate that the soft tissue be idealized first, and then the dental and skeletal changes be made to produce the ideal profile while correcting the bite. Based on the resulting hard numbers, the orthodontist and orthognathic surgeon will be guided with a precise treatment regimen which will allow ideal results to be achieved.

Methodology of past cephalometric analyses is flawed in other ways. As part of other cephalometric studies the lips were often closed distorting soft tissue to hard tissue relationships. Additionally, measurements were made relative to cranial base landmarks which are themselves extremely variable. Further, the standards developed in previous cephalometric studies have contained patients with skeletal and facial disharmony.

The drawings, tables, and attachments and the foregoing description are not intended to represent the only form of the invention in regard to the details of its methodology and manner of operation. In fact, it will be evident to one skilled in the art that modifications and variations may be made without departing from the spirit and scope of the invention. Although specific terms have been employed, they are intended in a generic and descriptive sense only and not for the purpose of limitation, and the invention is set forth in the following claims.

What is claimed is:

1. A method of soft tissue cephalometric analysis for aesthetic correction of facial imbalance in male and female patients, comprising:
   carrying out soft tissue cephalometric analysis comprising the steps of:
   establishing separate male and female databases of size and angle measurements of key facial landmarks and facial harmony values compiled from a group aesthetically balanced male and female faces;
   assessing the male or female patient's facial features by placing the patient's face in a natural head position, placing markers on facial structures, taking a headfilm image, and measuring size and angle measurements of key facial landmarks of the patient;
   localizing a true vertical line on the headfilm image;
   measuring absolute landmark values and angle measurements relative to the true vertical line and determining the patient's facial harmony values; and
   comparing the measured absolute landmark values and angle measurements and harmony values of the male or female patient to the corresponding database of size and angle measurements of key facial landmarks and facial harmony values.

2. The method of claim 1, wherein the step of assessing the male or female patient's facial features comprises:
   placing the patient's head in a natural head position, centric relationship, with passive lips;
   placing markers on one side of the patient's face on a plurality of facial structures including an orbital rim marker over osseous orbital rim and directly under pupil while in a straightahead gaze, a cheekbone marker on intersection of malar height and a vertical line through outer canthus, an alar base marker on deepest depression of alar base of nose, a subpupil marker directly below a straight gaze of pupil, and a neck-throat marker at neck-throat point at which throat breaks inferiorly to form neck; and
   taking a lateral headfilm image and marking hard and soft tissue cephalometric landmarks on the lateral headfilm image.

3. The method of claim 1, wherein the separate male and female databases of size and angle measurements of key facial landmarks values include dentoskeletal measurements, soft tissue measurements, facial length measurements, and horizontal projections of key facial features to the true vertical line.

4. The method of claim 3, wherein the dentoskeletal measurements include measurement of maxilla occlusal plane, maxilla incisor tip to occlusal plane, mandible incisor tip to occlusal plane, overjet, and overbite, wherein the soft tissue measurements include upper lip thickness, lower lip thickness, pogonion to pogonion' thickness, menton to menton' thickness, nasolabial angle, and upper lip angle, wherein the facial length measurements include nasion' to menton', upper lip length, interlabial gap, lower lip length, maxilla incisor exposure, mandibular height, overbite, maxillary height, and length of lower ⅓ of face, and wherein the horizontal measurements of key facial features to the true vertical line include glabella, orbital rim, cheek bone, subpupil, alar base, nasal projection, subnasal, A point', upper lip anterior, maxilla incisor tip, mandible incisor tip, lower lip anterior, B point', and pogonion'.

5. The method of claim 1, wherein the harmony values include intramandibular relations, interjaw relations, orbit to jaws, and full facial balance.

6. The method of claim 5, wherein the intramandibular relations include mandible incisor to pogonion', lower lip anterior to pogonion', neck throat point to pogonion', and B point' to pogonion', wherein the interjaw relations include subnasale' to pogonion', A point' to B point', and upper lip anterior to lower lip anterior, wherein the orbit to jaws relationship includes orbital rim' to A point' and orbital rim' pogonion', and wherein the full facial balance includes facial angle, glabella' to A point', and glabella' to pogonion'.

7. The method of claim 1, wherein the headfilm image is a lateral X-ray image and the markers are radiopaque spherical metallic beads.

8. The method of claim 1, further comprising the steps of carrying out cephalometric treatment planning including the steps of:
  correcting axial inclinations of maxillary incisors within the range of about 56.8±2.5 degrees to the maxilla occlusal plane for female patients within the range of about 57.8±3.0 degrees to the maxilla occlusal plane for male patients;
  correcting axial inclinations of mandillary incisors within the range of about 64.3±3.2 degrees to the mandible occlusal plane for female patients and within the range of about 64.0±4.0 degrees to the mandible occlusal plane for male patients;
  setting maxilla incisor position if required to bring within normal position range to expose about 3 to 5 mm below the upper lip;
  autorotating the mandible to the maxilla if necessary to correct any incorrect overbite;
  moving the mandible to correct any overjet with the maxillary arch;
  defining the maxillary occlusal plane; and
  assessing chin projection and changing if necessary to bring into normal ranges.

9. A method of soft tissue cephalometric analysis for diagnosis and cephalometric planning treatment for aesthetic correction of facial imbalance in male and female patients, comprising:
  (a) carrying out soft tissue cephalometric analysis comprising the steps of:
    establishing separate male and female databases of size and angle measurements of key facial landmarks and facial harmony values compiled from a group of aesthetically balanced male and female faces;
    assessing the male or female patient's facial features by placing the patient's face in a natural head position, placing markers on facial structures, taking a headfilm image, and measuring size and angle measurements of key facial landmarks of the patient;
    localizing a true vertical line on the headfilm image;
    measuring absolute landmark values and angle measurements relative to the true vertical line and determining the patient's facial harmony values; and
    comparing the measured absolute landmark values and angle measurements and harmony values of the male or female patient to the corresponding database of size and angle measurements of key facial landmarks and facial harmony values; and
  (b) carrying out cephalometric treatment planning comprising the steps of:
    correcting axial inclinations of maxillary incisors within the range of about 56.8±2.5 degrees to the maxilla occlusal plane for female patients within the range of about 57.8±3.0 degrees to the maxilla occlusal plane for male patients;
    correcting axial inclinations of mandillary incisors within the range of about 64.3±3.2 degrees to the mandible occlusal plane for female patients and within the range of about 64.0±4.0 degrees to the mandible occlusal plane for male patients;
    setting maxilla incisor position if required to bring within normal position range to expose about 3 to 5 mm below the upper lip;
    autorotating the mandible to the maxilla if necessary to correct any incorrect overbite;
    moving the mandible to correct any overjet with the maxillary arch;
    defining the maxillary occlusal plane; and
    assessing chin projection and changing if necessary to bring into normal ranges.

10. The method of claim 9, wherein the step of assessing the patient's facial features comprises:
  placing the patient's head in a natural head position, centric relationship, with passive lips;
  placing markers on one side of the patient's face on a plurality of facial structures including an orbital rim marker over osseous orbital rim and directly under pupil while in a straightahead gaze, a cheekbone marker on intersection of malar height and a vertical line through outer canthus, an alar base marker on deepest depression of alar base of nose, a subpupil marker directly below a straight gaze of pupil, and a neck-throat marker at neck-throat point at which throat breaks inferiorly to form neck; and
  taking a lateral headfilm image and marking hard and soft tissue cephalometric landmarks on the lateral headfilm image.

11. The method of claim 9, wherein the male and female databases of size and angle measurements of key facial landmarks values include dentoskeletal measurements, soft tissue measurements, facial length measurements, and horizontal projections of key facial features to the true vertical line.

12. The method of claim 11, wherein the dentoskeletal measurements include measurement of maxilla occlusal plane, maxilla incisor tip to occlusal plane, mandible incisor tip to occlusal plane, overjet, and overbite, wherein the soft tissue measurements include upper lip thickness, lower lip thickness, pogonion to pogonion' thickness, menton to menton' thickness, nasolabial angle, and upper lip angle, wherein the facial length measurements include nasion' to menton', upper lip length, interlabial gap, lower lip length, maxilla incisor exposure, mandibular height, overbite, maxillary height, and length of lower ⅓ of face, and wherein the horizontal measurements of key facial features to the true vertical line include glabella, orbital rim, cheek bone, subpupil, alar base, nasal projection, subnasal, A point', upper lip anterior, maxilla incisor tip, mandible incisor tip, lower lip anterior, B point', and pogonion'.

13. The method of claim 9, wherein the harmony values include intramandibular relations, interjaw relations, orbit to jaws, and full facial balance.

14. The method of claim 9, wherein the intramandibular relations include mandible incisor to pogonion', lower lip anterior to pogonion', neck throat point to pogonion', and B point' to pogonion', wherein the interjaw relations include subnasale' to pogonion', A point' to B point', and upper lip anterior to lower lip anterior, wherein the orbit to jaws relationship includes orbital rim' to A point' and orbital rim' pogonion', and wherein the full facial balance includes facial angle, glabella' to A point', and glabella' to pogonion'.

15. The method of claim 9, wherein the headfilm image is a lateral X-ray image and the markers are radiopaque spherical metallic beads.

* * * * *